United States Patent [19]

Holzhauer et al.

[11] Patent Number: 4,886,901

[45] Date of Patent: Dec. 12, 1989

[54] METHOD FOR PURIFYING A CRUDE DIMETHYL NAPHTHALENE DICARBOXYLATE

[75] Inventors: Juergen K. Holzhauer, Naperville; Robert D. Oltrogge, Lombard; Dennis J. Michalak, Warrenville, all of Ill.

[73] Assignee: Amoco Corporation, Chicago, Ill.

[21] Appl. No.: 274,238

[22] Filed: Nov. 21, 1988

[51] Int. Cl.$^4$ .................... C07C 67/48; C07C 67/39
[52] U.S. Cl. ........................ 560/77; 560/78; 560/80
[58] Field of Search ............... 560/77, 78, 80

[56] References Cited

U.S. PATENT DOCUMENTS

| | | | |
|---|---|---|---|
| 3,334,131 | 8/1967 | Burkhardt | 560/78 |
| 3,402,195 | 9/1968 | Barna | 560/78 |
| 3,425,915 | 2/1969 | Roberts et al. | 560/78 X |
| 3,962,315 | 6/1976 | Achsel et al. | 560/78 |
| 4,048,021 | 9/1977 | Takamoto et al. | 560/78 X |
| 4,126,755 | 11/1978 | Bunger et al. | 560/77 |

Primary Examiner—Werren B. Lone
Assistant Examiner—Vera C. Clarke
Attorney, Agent, or Firm—James R. Henes; William H. Magidson; Ralph H. Medhurst

[57] ABSTRACT

A method for purifying a dimethyl naphthalene dicarboxylate produced from a naphthalene dicarboxylic acid which is in turn produced by the liquid phase oxidation of a dialkylnaphthalene or partially oxidized derivative thereof in the presence of a catalyst comprising a bromine-containing component and at least one of a cobalt- or manganese-containing component.

21 Claims, No Drawings 4,886,901

METHOD FOR PURIFYING A CRUDE DIMETHYL NAPHTHALENE DICARBOXYLATE

BACKGROUND OF THE INVENTION

1. Field of the Invention

This invention relates generally to a method for purifying a crude dimethyl naphthalene dicarboxylate and more particularly concerns a method for purifying a crude dimethyl naphthalene dicarboxylate produced from a naphthalene dicarboxylic acid which is produced by the liquid-phase oxidation of a dialkylnaphthalene or partially oxidized derivative thereof in a solvent.

2. Discussion of the Prior Art

Fibers and films produced from polyethylenenaphthalate have improved strength and thermal properties relative to fibers and films produced from polyethyleneterephthalate and are especially useful in applications such as tire cords, magnetic tape backings and hot-fill containers. Naphthalene dicarboxylic acid, especially 2,6-naphthalene dicarboxylic acid, is employed as a monomer in the production of polyethylene naphthalate and is typically prepared by the catalyzed, liquid-phase oxidation of a dialkylnaphthalene, especially 2,6-dialkylnaphthalene.

The presence of impurities in the naphthalene dicarboxylic acid can obviously have a serious adverse effect on the physical or chemical properties or performance characteristics of any formulation containing the naphthalene dicarboxylic acid itself or any polymer formed from the naphthalene dicarboxylic acid. In addition, impurities in the naphthalene dicarboxylic acid can adversely affect polymerization processes to which the naphthlene dicarboxylic acid is subjected. Such impurities in the naphthalene dicarboxylic acid formed by the catalyzed, liquid-phase oxidation of a dialkylnaphthalene or partially oxidized derivative thereof are often organic impurities or by-products formed during the oxidation and inorganic impurities corresponding to metal components of the catalysts employed in the oxidation or formed therefrom.

Thus, removal of such impurities from the naphthalene dicarboxylic acid is highly desirable. However, the removal of organic and inorganic impurities from aromatic polycarboxylic acids formed by the catalyzed, liquid-phase oxidation of polyalkyl aromatics is typically very difficult, and the removal technique employed depends on the specific aromatic polycarboxylic acid from which the impurities are to be removed and the specific oxidation conditions and catalyst employed to make it.

In particular, naphthalene dicarboxylic acids are especially difficult to purify because of their low solubility in many solvents. Formation of the methyl ester is the best method known for purifying a naphthalene dicarboxylic acid. However, formation of the methyl ester alone does not afford a sufficiently pure monomer. Therefore, the methyl ester itself must be further purified, which purification can be time consuming and involve relatively complex reaction schemes.

OBJECTS OF THE INVENTION

It is therefore a general object of the present invention to provide an improved method which overcomes the aforesaid problems of prior art methods for purifying crude dimethyl naphthalene dicarboxylate produced from naphthalene dicarboxylic acid produced by the liquidphase oxidation of a dialkylnaphthalene or partially oxidized derivative thereof with an oxygen-containing gas in a solvent and in the presence of an oxidation catalyst comprising a bromine-containing component and at least one cobalt- or manganese-containing component.

More particularly, it is an object of the present invention to provide a fast and simple method for purifying crude dimethyl naphthalene dicarboxylate produced from naphthalene dicarboxylic acid produced by the aforesaid liquid-phase oxidation of a dialkylnaphthalene or partially oxidized derivative thereof which affords a purified dimethyl naphthalene dicarboxylate product having reduced contents of organic and inorganic impurities.

Other objects and advantages of the invention will become apparent upon reading the following detailed description and appended claims.

SUMMARY OF THE INVENTION

These objects are achieved by the present invention which is an improvement in a method for producing a dimethyl naphthalene dicarboxylate comprising oxidizing a dialkylnaphthalene wherein each alkyl group may be the same or different and is methyl, ethyl, propyl, or a partially oxidized derivative thereof, with an oxygen-containing gas in a solvent in the liquid phase at an elevated temperature and pressure and in the presence of an oxidation catalyst comprising a bromine component and at least one of a cobalt- or manganese-containing component to form a crude naphthalene dicarboxylic acid, and esterifying the resulting crude naphthalene dicarboxylic acid with methanol in the presence of an esterification catalyst at an elevated temperature and pressure to form a crude dimethyl naphthalene dicarboxylate. The improvement comprises purifying the resulting crude dimethyl naphthalene dicarboxylate by (a) washing the crude dicarboxylate with an alkylated or halogenated aromatic having a normal boiling point of less than 175° C. at a weight ratio in the range of from about 0.25 to about 5 parts of the alkylated or halogenated aromatic per part by weight of the dicarboxylate to remove at least a substantial portion of the residual methanol and colored impurities, wherein optionally a base comprising a hydroxide, carbonate or bicarbonate of an alkali or alkaline earth metal is added at a weight ratio in the range of from about 0.001 to about 0.1 of the base per part by weight of the dicarboxylate; (b) combining the washed dicarboxylate with an alkylated or halogenated aromatic having a normal boiling point of less than 175° C., at a weight ratio of from about 2 to about 10 parts of alkylated or halogenated aromatic per part of the dicarboxylate, wherein optionally the aforesaid base is added at a weight ratio in the range of from about 0.001 to about 0.1 part of the base per part by weight of the dicarboxylate; (c) mixing the resulting combination at a temperature range of from about 65° C. to about 115° C. with water at a weight ratio in the range of from about 0.02 to about 0.3 part of water per part by weight of dicarboxylate, wherein optionally the aforesaid base is added at a weight ratio in the range of from about 0.001 to about 0.1 part of the base per part by weight of the dicarboxylate; (d) heating the resulting liquid mixture to a temperature in the range of from about 100° C. to about 140° C. to distill off the water and to dissolve substantially all of the dicarboxylate in the alkylated or halogenated aromatic combined in step (b); (e) introducing to the resulting water-free solution in the alkylated or halogenated aromatic an alkali alkoxide containing up to 4 carbon atoms at a weight ratio of from about 0.001 to about 0.02 part of the alkoxide per part by weight of the dicarboxylate; (f) removing solids from the resulting mixture at a temperature in the range of from about 120° C. to about 150° C.; (g) crystallizing the dicarboxylate by cooling the solid-free solution to a temperature in the range of from about 0° C. to about 50° C. with agitation; and (h) separating the resulting purified dimethyl naphthalene dicarboxylate crystals from the liquid alkylated or halogenated aromatic.

DETAILED DESCRIPTION OF THE PREFERRED EMBODIMENTS

Any dialkylnaphthalene wherein the alkyl substituent contains from 1 to 3 carbon atoms or the partially oxidized derivative thereof, is suitable for use as the feedstock in the oxidation step of the method of this invention. Suitable partially oxidized derivatives include formylmethylnaphthalene, acetylmethylnaphthalene, carboxymethylnaphthalene, diformylnaphthalene, diacetylnaphthalene, and dicarboxynaphthalene. Preferably, the oxidizable substituents are in the 2,6-position on the naphthalene ring. Preferably, the alkyl group is a methyl group, and, more preferably, the feedstock is a dimethylnaphthalene. Most preferably, the feedstock is 2,6-dimethylnaphthalene.

Suitable solvents for use in the oxidation step of the method of this invention include benzoic, any aliphatic $C_2$–$C_6$ monocarboxylic acid such as acetic acid, propionic acid, n-butyric acid, isobutyric acid, n-valeric acid, trimethylacetic acid, and caproic acid, and water, and mixtures thereof. Preferably, the solvent is a mixture of acetic acid and water, which more preferably contains from 1 to 20 weight percent of water, as introduced into the oxidation reactor. Since heat generated in the highly exothermic liquid-phase oxidation is dissipated at least partially by vaporization of solvent in the oxidation reactor, some of the solven is withdrawn from the oxidation reactor as a vapor, which is then condensed and recycled to the reactor.

In addition, some solvent is withdrawn from the oxidation reactor as a liquid in the product stream. After separation of the crude naphthalene dicarboxylic acid product from the product stream, at least a portion of the mother liquor (solvent) in the resulting product stream is generally recycled to the oxidation reactor.

The source of molecular oxygen employed in the oxidation step of the method of this invention can vary in molecular oxygen content from that of air to oxygen gas. Air is the preferred source of molecular oxygen. In order to avoid the formation of explosive mixtures, the oxygen-containing gas fed to the reactor should provide an exhaust gas-vapor mixture containing from 0.5 to 8 volume percent oxygen (measured on a solvent-free basis). For example, a feed rate of the oxygen-containing gas sufficient to provide oxygen in the amount of from 1.5 to 2.8 moles per methyl group will provide such 0.5 to 8 volume percent of oxygen (measured on a solvent-free basis) in the gas-vapor mixture in the condenser.

The catalyst employed in the oxidation step of the method of this invention comprises a bromine-containing component and at least one of a cobalt- and manganese-containing component, and can additionally comprise accelerators known in the art. Preferably, the catalyst comprises cobalt-, manganese-, and bromine-containing components. The weight ratio of cobalt (calculated as elemental cobalt) in the cobalt component of the catalyst-to the dialkylnaphthalene or partially oxidized derivative thereof in the liquid-phase oxidation is in the range of from about 0.1 to about 10 milligram atoms (mga) per gram mole of dialkylnaphthalene or partially oxidized derivative thereof. The weight ratio of manganese (calculated as elemental manganese) in the manganese component of the catalyst-to-cobalt (calculated as elemental cobalt) in the cobalt component of the catalyst in the liquid-phase oxidation is in the range of from about 0.1 to about 10 mga per mga of cobalt. The weight ratio of bromine (calculated as elemental bromine) in the bromine component of the catalyst-to-total cobalt and manganese (calculated as elemental cobalt and elemental manganese) in the cobalt and manganese components of the catalyst in the liquid-phase oxidation is in the range of from about 0.1 to about 1.5 mga per mga of total cobalt and manganese.

Each of the cobalt and manganese components can be provided in any of its known ionic or combined forms that provide soluble forms of cobalt, manganese, and bromine in the solvent in the reactor. For example, when the solvent is an acetic acid medium, cobalt and/or manganese carbonate, acetate tetrahydrate, and/or bromide can be employed. The 0.1:1.0 to 1.5:1.0 bromine-to-total cobalt and manganese milligram atom ratio is provided by a suitable source of bromine. Such bromine sources include elemental bromine ($Br_2$), or ionic bromide (e.g., HBr, NaBr, KBr, $NH_4Br$, etc.), or organic bromides which are known to provide bromide ions at the operating temperature of the oxidation (e.g., bromobenzenes, benzyl-bromide, mono- and di-bromoacetic acid, bromoacetyl bromide, tetrabromoethane, ethylene-di-bromide, etc.). The total bromine in molecular bromine and ionic bromide is used to determine satisfaction of the elemental bro- mine-to-total cobalt and manganese milligram atom ratio of 0.1:1.0 to 1.5:1.0. The bromine ion released from the organic bromides at the oxidation operating conditions can be readily determined by known analytical means. Tetrabromoethane, for example, at operating temperatures of 170° C. to 225° C. has been found to yield about 3 effective gram atoms of bromine per gram mole.

In operation, the minimum pressure at which the oxidation reactor is maintained is that pressure which will maintain a substantial liquid phase of the dialkyl naphthalene or partially oxidized derivative thereof and at least 70 percent of the solvent. The dialkyl naphthalene or partially oxidized derivative thereof and solvent not in the liquid phase because of vaporization is removed from the oxidation reactor as a vapor-gas mixture, condensed, and then returned to the oxidation reactor. When the solvent is an acetic acid-water mixture, suitable reaction gauge pressures in the oxidation reactor are in the range of from about 0 kg/$cm^2$ to about 35 kg/$cm^2$, and typically are in the range of from about 10 kg/$cm^2$ to about 30 kg/$cm^2$. The temperature range within the oxidation reactor is generally from about 120° C., preferably from about 150° C., to about 240° C., preferably to about 230° C. The solvent residence time in the oxidation reactor is generally from about 20 to about 150 minutes and preferably from about 30 to about 120 minutes.

The oxidation of the method of this invention can be performed either on a batch, continuous, or semi-continuous mode. In the batch mode, the dialkylnaphthalene or its partially oxidized derivative, solvent and the catalyst components are initially introduced batchwise into the reactor, and the temperature and pressure of the reactor contents are then raised to the desired levels therefor for the commencement of the oxidation reaction. Air is introduced continuously into the reactor. After commencement of the oxidation reaction—for example, after all of the dialkylnaphthalene or its partially oxidized derivative has been completely introduced into the reactor, the temperature of the reactor contents is raised.

In the continuous mode, each of the dialkyl naphthalene or partially oxidized derivative thereof, air, solvent, and catalyst are continuously introduced into the reactor, and a product stream comprising naphthalene dicarboxylic acid and catalyst components dissolved in the solvent is withdrawn from the reactor. In the semi-continuous mode, the solvent and catalyst are initially introduced into the reactor and then the dialkyl naphthalene or its partially oxidized derivative and air are continuously introduced into the reactor.

Thereafter, the product stream in the continuous mode or the reactor contents in the batch or semicontinuous mode are cooled to a temperature in the range of from about 80° C. to about 105° C. in at least one step and in at least one crystallizer such that essentially all of the naphthalene dicarboxylic acid crystallizes in the solvent. Following crystallization, the resulting slurry of naphthalene dicarboxylic acid in the mother liquor is separated, typically by centrifugation, at a temperature in the range of from about 80° C. to about 105° C. Generally the separation is performed at essentially the same temperature as the final crystallization temperature.

The resulting separated crude naphthalene dicarboxylic acid is converted to its dimethyl ester by esterification with methanol in the presence of an esterification catalyst at an elevated temperature and pressure. Any convenient, conventional such esterification procedure can be employed. Suitably, the esterification catalyst is sulfuric acid, p-toluene sulfonic acid, methane sulfonic acid, a titanium alkoxide, zinc, zinc oxide, molybdenum trioxide, or organic tin compounds. Typically, the crude naphthalene dicarboxylic acid, methanol and an 80–85 weight percent solution of sulfuric acid in water are mixed in a weight ratio of 1:8:0.1 and heated to 120° C. with agitation and held at that temperature for about 6 hours. The mixture is then cooled to a temperature between 20° C. and 65° C. to crystallize the dimethyl naphthalene dicarboxylate, and the resulting crude dimethyl naphthalene dicarboxylate is separated from the mother liquor for example, by centrifugation. A methanol wash may be used to remove sulfuric acid. Continuous esterification, crystallization and vacuum filtration may also be employed.

The resulting crude dimethyl naphthalene dicarboxylate is then purified in accordance with the improvement of the method of this invention. First, in step (a), the crude dicarboxylate is washed (or equivalently, dispersed) with a suitable alkylated or halogenated aromatic having a normal boiling point of less than 175° C., such as a xylene, toluene, pseudocumene, ethylbenzene, or chlorobenzene, at a weight ratio of from about 0.25, preferably from about 0.5, to about 5, preferably to about 3, parts of the alkylated or halogenated aromatic per part by weight of the dicarboxylate, to thereby remove at least a substantial portion of the residual methanol and the colored impurities. Optionally a base comprising a hydroxide, carbonate or bicarbonate of an alkali or alkaline earth metal is also added in this step at a weight ratio in the range of from about 0.001, preferably from about 0.005, to about 0.1 preferably to about 0.06 part of the base per part by weight of the dicarboxylate. Typically, the base is a calcium, barium, potassium, sodium or lithium hydroxide, carbonate or bicarbonate.

In step (b), the resulting washed dicarboxylate is combined with an aforesaid alkylated or halogenated aromatic at a weight ratio of from about 2, preferably from about 3, to about 10, preferably to about 7 parts of the alkylated or halogenated aromatic per part by weight of the dicarboxylate. The combination is effected at a temperature in the range of from about 65° C. preferably from about 75° C., to about 115° C., preferably to about 105° C., under which conditions the dicarboxylate generally does not dissolve entirely. In the alternative, the dicarboxylate can be dissolved in the alkylated or halogenated aromatic by heating the combination to a temperature in the range of from about 116° C., preferably from about 120° C., to about 140° C., preferably to about 130° C., and then cooled to a temperature in the range of from about 65° C., preferably from about 75° C., to about 115° C., preferably to about 105° C. Optionally a base comprising a hydroxide, carbonate or bicarbonate of an alkali or alkaline earth metal is also added in this step at a weight ratio in the range of from about 0.001, preferably from about 0.005, to about 0.1, preferably to about 0.06 part of the base per part by weight of the dicarboxylate. Typically, the base is a calcium, barium, potassium, sodium or lithium hydroxide, carbonate or bicarbonate.

In step (c), the resulting combination is mixed with water in a weight ratio in the range of from about 0.02, preferably from about 0.04, to about 0.3, preferably to about 0.2 part of water per part by weight of dicarboxylate at a temperature in the range of from about 65° C,. preferably from about 75° C., to about 115° C., preferably to about 105° C. Preferably the mixing is performed for from about 0.1 to about 4 hours. Optionally a base comprising a hydroxide, carbonate or bicarbonate of an alkali or alkaline earth metal is also added in this step at a weight ratio in the range of from about 0.001, preferably from about 0.005, to about 0.1, preferably to about 0.06 part of the base per part by weight of the dicarboxylate. Typically, the base is a calcium, barium, potassium, sodium or lithium hydroxide, carbonate or bicarbonate.

In at least one of steps (a), (b) and (c), an aforesaid base is added either preferably as a solid or as dissolved in water both. The total amount of base added in steps (a), (b) and (c) combined is in the range of from about 0.001, preferably from about 0.005, to about 0.1, preferably to about 0.06, parts of base per part by weight of the dicarboxylate. Preferably base, more preferably all of the base, is added in step (b).

In step (d), the resulting liquid mixture is heated to a temperature in the range of from about 100° C., preferably from about 110° C., to about 140° C., preferably to about 130° C. to distill off the water and to completely dissolve the dicarboxylate in the alkylated or halogenated aromatic.

In step (e), an alkali alkoxide containing up to 4 carbon atoms is introduced into the resulting water-free alkylated or halogenated aromatic solution at a weight ratio in the range of from about 0.001, preferably from about 0.002, to about 0.02, preferably to about 0.01, part of the alkoxide per part by weight of the dicarboxylate in the solution. Preferably, the alkoxide is sodium methoxide. Preferably the alkoxide is added as dissolved in methanol. If flashing of methanol is undesirable, the methanol solution is introduced under conditions of temperature or pressure or both such that the methanol is not flashed off. For example, either the water-free alkylated halogenated aromatic solution could be cooled to a temperature in the range of from about 20° C., preferably from about 60° C., to about 80° C., preferably to about 70° C., or the methanol solution could be introduced at a higher temperature but under the surface of the alkylated or halogenated aromatic solution or under a pressure in the range of from about 1, preferably from about 2, to about 10, preferably to about 5 atmospheres absolute.

In step (f), the resulting liquid mixture is heated to, and solids are removed at, for example, by filtration, a temperature in the range of from about 120° C., preferably from about 125° C., to about 150° C., preferably to about 145° C. to distill off the methanol. Preferably a filter aid such as Celite is employed in such filtration. For example, the filter could be precoated with a filter aid.

In step (g), the resulting solid-free solution is cooled to a temperature in the range of from about 0° C., preferably from about 10° C., to about 50° C., preferably to about 40° C. with agitation to crystallize the resulting purified dicarboxylate, which is then separated and recovered in step (h), for example, by filtration or centrifugation.

In a preferred embodiment of the method of this invention, prior to step (f), activated carbon is admixed with the dicarboxylate at a weight ratio in the range of from about 0.005, preferably from about 0.01, to about 0.05, preferably to about 0.04 part of activated carbon per part by weight of dicarboxylate and is separated from the liquid in step (f). More preferably, the treatment with activated carbon is effected after step (b).

In a further preferred embodiment of the method of this invention, the purified dicarboxylate from step (h) is washed with methanol or an aforesaid alkylated or halogenated mene, ethylbenzene, or chlorobenzene.

Finally, the recovered and optionally washed purified dimethyl naphthalene dicarboxylate is dried to remove all liquids therefrom.

The present invention will be more clearly understood from the following specific examples.

EXAMPLE 1

Crude dimethyl naphthalene dicarboxylate comprising 100 grams of solids and 84.4 grams of liquid (primarily methanol) was slurried with 200 grams of xylene for 5 minutes and filtered, and the resulting cake was washed with 50 grams of xylene.

The washed cake, 400 grams of xylene and 4 grams of calcium hydroxide were charged to flask equipped with a heater, stirrer, condenser and thermocouple and heated to 90° C. The temperature of the mixture was lowered to 85° C. by adding 15 grams of cold water, and the mixture was agitated at 85° C. for one hour. The mixture was then heated to distill off the water as a component in its azeotropic mixture with xylene. When the temperature reached 120° C., a solution of 0.5 grams of sodium methoxide in 4.5 grams of methanol was injected below the liquid level by means of a syringe. The resulting mixture was heated to 130° C. while distilling off the methanol.

Three grams of Nuchar SN activated carbon and 7 grams of Celite Hyflo filter aid were added to the liquid, and the resulting mixture was heated to 140° C. and filtered through a preheated filter which has been precoated with Celite to obtain a filtrate. The filter was washed twice, each time with 50 grams of boiling xylene, with the first wash filtrate being combined with the aforesaid filtrate, and with the second wash filtrate being set aside.

The dicarboxylate was crystallized from the aforesaid combined filtrates by cooling to room temperature with agitation. The resulting crystals were separated and recovered by filtration.

The resulting filter cake was washed first with the aforesaid filtrate that had been set aside and then with 50 grams of fresh xylene. The wet cake was dried for 16 hours at 110° C. and under 0.33 atmosphere of pressure. 85.4 grams of dry purified dimethyl naphthalene dicarboxylate were recovered.

Some of the reaction conditions employed in, and the characteristics of the purified dicarboxylate produced in, Example 1, as well as in Examples 2-5, are summarized in Table 1.

In Table 1, YIE represents the yellowness index and is a measure of the yellowness of a chloroform solution of the dimethyl naphthalene dicarboxylate and is based on ASTM Method E-313, "Indices of Whiteness and Yellowness of Near-white, Opaque Materials." YIE is related to B (blue reflectance or transmission) and G (green reflectance or transmission) values. With B and G values expressed in percent, YIE is calculated as $$YIE = 100 (1 - B/G)$$

The measurements were made using a Gardner XL-835 tri-stimulus colorimeter.

The color of the dimethyl ester product in Example 1 was exceptionally good.

TABLE 1

| Process Variable | Example No. | | | | |
|---|---|---|---|---|---|
|  | 1 | 2 | 3 | 4 | 5 |
| Wash of the crude ester | yes | yes | yes | yes | no |
| Sodium methoxide treatment | yes | no | yes | yes | yes |
| Activated carbon treatment | yes | yes | no | no | no |
| Reslurry/wash of purified ester | yes | yes | yes | no | no |
| Product Characteristics | | | | | |
| YIE | 0.05 | 0.31 | 0.13 | 0.27 | 0.56 |
| Acid No. (mg KOH/g) |  | <0.05 | <0.05 | <0.05 | <0.05 |
| Haze (National Turbidy Units) |  | 0.35 | 0.16 | 0.16 | 0.23 |

EXAMPLE 2

The apparatus, procedure and conditions employed in Example 1 were also employed in Example 2, except that the sodium methoxide treatment was not employed in Example 2, which therefore is a comparative example. The color of the product from Example 2 was substantially increased relative to the color of the product of Example 1.

EXAMPLE 3

Crude dimethyl naphthalene dicarboxylate comprising 50 grams of solids and 42.2 grams of liquid was slurried in 125 grams of xylene and filtered. The resulting wet cake, 250 grams of xylene and 1.5 grams of calcium hydroxide were charged to a 1-liter resin kettle. The mixture was heated to 120° C. to dissolve the dicarboxylate and then cooled to 85° C. 6 grams of water were added, and the resulting mixture was agitated at 85° C. for 30 minutes. The mixture was then heated to 130° C. over a period of 45 minutes to distill off the water, after which the mixture was cooled to 60° C., at which temperature a solution of 0.25 gram of sodium methoxide in 0.75 gram of methanol was added by pouring it onto the liquid surface. The resulting mixture was then heated to 130° C. to distill off the methanol and then filtered through a preheated filter that had been precoated with a filter aid. The filter was washed with 50 milliliters of xylene at 130° C. The purified dimethyl naphthalene dicarboxylate was crystallized by cooling the combined total filtrate to room temperature with agitation. The resulting wet cake was reslurried in 100 grams of xylene, filtered and dried to afford 43.3 grams of dry purified dimethyl naphthalene dicarboxylate. The color of the resulting product was especially good.

EXAMPLE 4

The apparatus, procedure and conditions employed in Example 3 were also employed in Example 4, except that the purified dimethyl naphthalene dicarboxylate product was not reslurried. The color of the resulting product was relatively worse than the color of the product from Example 3 but the acid numbers and haze characteristics of the two products were essentially the same.

EXAMPLE 5

The apparatus, procedure and conditions employed in Example 4 were employed in Example 5, except that the wash of the crude dicarboxylate in xylene was omitted, and thus Example 5 is a comparative example. The color characteristics of this product were the worst of the products made.

From the above description, it is apparent that the objects of the present invention have been achieved. While only certain embodiments have been set forth, alternative embodiments and various modifications will be apparent from the above description to those skilled in the art and are considered equivalent and within the spirit and scope of the present invention.

Having described the invention, what is claimed is:

1. In a method for producing a dimethyl naphthalene dicarboxylate comprising oxidizing a dialkylnaphthalene wherein each alkyl group may be the same or different and is methyl, ethyl or propyl, or a partially oxidized derivative thereof, with an oxygen-containing gas in a solvent in the liquid phase at an elevated temperature and pressure and in the presence of an oxidation catalyst comprising a bromine component and at least one of a cobalt- or manganese-containing component to form a crude naphthalene dicarboxylic acid, and esterifying the resulting crude naphthalene dicarboxylic acid with methanol in the presence of an esterification catalyst at an elevated temperature and pressure to form a crude dimethyl naphthalene dicarboxylate: the improvement comprising purifying the resulting crude dimethyl naphthalene dicarboxylate by:
   (a) washing the crude dicarboxylate with an alkylated or halogenated aromatic having a normal boiling point of less than 175° C., at a weight ratio in the range of from about 0.25 to about 5 parts of the alkylated or halogenated aromatic per part by weight of the dicarboxylate, to remove at least a substantial portion of the residual methanol and colored impurities, wherein optionally a base comprising a hydroxide, carbonate or bicarbonate of an alkali or alkaline earth metal is added at a weight ratio in the range of from about 0.001 to about 0.1 of the base per part by weight of the dicarboxylate;
   (b) combining the washed dicarboxylate with an alkylated or halogenated aromatic having a normal boiling point of less than 175° C., at a weight ratio of from about 2 to about 10 parts of alkylated or halogenated aromatic per part ally the aforesaid base is added at a weight ratio in the range of from about 0.001 to about 0.1 part of the base per part by weight of the dicarboxylate;
   (c) mixing the resulting combination at a temperature in the range of from about 65° C. to about 115° C. with water at a weight ratio in the range of from about 0.02 to about 0.3 part of water per part by weight of the dicarboxylate, wherein optionally the aforesaid base is added at a weight ratio in the range of from about 0.001 to about 0.1 part of the base per part by weight of the dicarboxylate, wherein the aforesaid base is added in at least one of steps (a), (b) and (c) at a total weight ratio in the range of from about 0.001 to about 0.1 part of the base per part by weight of the dicarboxylate;
   (d) heating the resulting liquid mixture to a temperature in the range of from about 100° C. to about 140° C. to distill off the water and to dissolve substantially all of the dicarboxylate in the alkylated or halogenated aromatic combined in step (b);
   (e) introducing to the resulting water-free solution in the alkylated or halogenated aromatic an alkali alkoxide containing up to 4 carbon atoms at a weight ratio of from about 0.001 to about 0.02 part of the alkoxide per part by weight of the dicarboxylate;
   (f) removing solids from the resulting mixture at a temperature in the range of from about 120° C. to about 150° C.;
   (g) crystallizing the dicarboxylate by cooling the resulting solid-free solution to a temperature in the range of from about 0° C. to about 50° C. with agitation; and
   (h) separating the resulting purified dimethyl naphthalene dicarboxylate crystals from the liquid alkylated or halogenated aromatic.

2. The method of claim 1 wherein, prior to step (f), activated carbon is admixed with the dicarboxylate at a weight ratio in the range of from about 0.005 to about 0.05 part of the activated carbon per part by weight of dicarboxylate.

3. The method of claim 1 wherein the purified dimethyl naphthalene dicarboxylate from step (h) is washed with methanol or an alkylated or halogenated aromatic having a normal boiling point of less than 175° C.

4. The method of claim 1 wherein the purified dimethyl naphthalene dicarboxylate from step (h) is dried.

5. The method of claim 1 wherein the alkylated or halogenated aromatic employed in step (a) or (b) or both is a xylene, chlorobenzene, ethylbenzene, toluene, or pseudocumene.

6. The method of claim 1 wherein the alkylated or halogenated aromatic in step (a) is employed at a weight ratio in the range of from about 0.5 to about 3 parts per part by weight of dicarboxylate.

7. The method of claim 1 wherein the alkylated or halogenated aromatic employed in step (b) is at a weight ratio in the range of from about 3 to about 7 parts of the alkylated or halogenated aromatic per part by weight of dicarboxylate.

8. The method of claim 1 wherein dicarboxylate and aromatic are combined in step (b) at a temperature in the range of from about 65° C. to about 115° C.

9. The method of claim 1 wherein the dicarboxylate and aromatic are combined in step (b) at a temperature in the range of from about 116° C. to about 140° C. and then cooled to a temperature in the range of from about 65° C. to about 115° C.

10. The method of claim 1 wherein in step (c) from about 0.04 to about 0.2 part of water are mixed with a part by weight of the dicarboxylate.

11. The method of claim 1 wherein in step (c) mixing is effected at a temperature in the range of from about 75° C. to about 105° C.

12. The method of claim 1 wherein the total amount of the base employed in steps (a), (b), and (c) is at a weight ratio in the range of from about 0.005 to about 0.06 part by weight of the base per part of dicarboxylate.

13. The method of claim 1 wherein the base employed in steps (a), (b), and (c) is calcium, barium, sodium, potassium, or lithium hydroxide, carbonate or bicarbonate.

14. The method of claim 1 wherein base is added in step (b).

15. The method of claim 1 wherein in step (d) the mixture is heated to a temperature in the range of from about 110° C. to about 130° C.

16. The method of claim 1 wherein the alkali alkoxide is introduced in step (e) at a weight ratio in the range of from about 0.002 to about 0.01 part of the alkoxide per part by weight of the dicarboxylate.

17. The method of claim 1 wherein the alkali alkoxide introduced in step (e) is sodium methoxide.

18. The method of claim 1 wherein in step (e) the alkali alkoxide is introduced as dissolved in methanol.

19. The method of claim 1 wherein the mixture in step (f) is heated at a temperature in the range of from about 125° C. to about 145° C.

20. The method of claim 1 wherein the solid-free solution is cooled to a temperature in the range of from about 10° C. to about 40° C. in step (g).

21. The method of claim 2 wherein the activated carbon is admixed after step (b).

* * * * *

UNITED STATES PATENT AND TRADEMARK OFFICE
CERTIFICATE OF CORRECTION

PATENT NO. : 4,886,901

DATED : December 12, 1989

INVENTOR(S) : Juergen K. Holzhauer, Robert D. Oltrogge & Dennis J. Michalak

It is certified that error appears in the above-identified patent and that said Letters Patent is hereby corrected as shown below:

| Col. | Line | |
|---|---|---|
| 1 | 68 | "liquidphase" should read --liquid-phase-- |
| 3 | 39 | "solven" should read --solvent-- |
| 4 | 2 | "catalyst-to the" should read --catalyst-to-the-- |
| 4 | 32 | "benzyl-bromide" should read --benzylbromide-- |
| 4 | 36 | "bro- mine" should read --bromine-- |
| 7 | 40 | "halogenated mene, ethylbenzene" should read --halogenated aromatic such as a xylene, toluene, pseudocumene, ethylbenzene-- |
| 10 | 9 | "ally" should read --by weight of the dicarboxylate, wherein optionally-- |

Signed and Sealed this

Twenty-second Day of January, 1991

Attest:

HARRY F. MANBECK, JR.

*Attesting Officer*    *Commissioner of Patents and Trademarks*